US000001363H

United States Statutory Invention Registration [19]

[11] Reg. Number: H1363

Leeker

[43] Published: Oct. 4, 1994

[54] FOLD AND WRAP PACKAGE FOR CATAMENIAL PADS PROVIDING CONVENIENT DISPOSAL

[76] Inventor: Karen K. Leeker, 6100 Center Hill Rd., Cincinnati, Ohio 45224

[21] Appl. No.: 994,843

[22] Filed: Dec. 22, 1992

[51] Int. Cl.[5] ..... A61F 13/16; A61F 13/18; B65D 85/00

[52] U.S. Cl. ..... 206/440; 206/225; 383/210; 604/358

[58] Field of Search ..... 206/0.82, 225, 438, 206/440, 494; 229/87.15; 383/84, 85, 86, 210, 211

[56] References Cited

U.S. PATENT DOCUMENTS

| | | | |
|---|---|---|---|
| 611,373 | 9/1898 | Blackman et al. | 206/225 |
| 3,035,578 | 8/1958 | Elmore . | |
| 3,062,371 | 11/1962 | Patience | 206/440 |
| 3,193,181 | 7/1965 | Konjevich et al. | 229/87.15 |
| 3,332,549 | 7/1967 | Powell | 383/210 |
| 3,348,762 | 10/1967 | Kasinkas | 383/86 |
| 3,674,195 | 7/1972 | Stone . | |
| 3,698,549 | 10/1972 | Glassman | 383/211 |
| 3,967,729 | 7/1976 | Tanner, II . | |
| 3,970,087 | 7/1976 | Castaneda . | |
| 3,973,567 | 8/1976 | Srinivasan et al. . | |
| 4,221,221 | 9/1980 | Ehrlich . | |
| 4,286,639 | 9/1981 | Murphy . | |
| 4,312,085 | 1/1982 | Potter . | |
| 4,402,689 | 9/1983 | Baum . | |
| 4,481,243 | 11/1984 | Allen . | |
| 4,546,875 | 10/1985 | Zweber | 206/0.2 |
| 4,555,022 | 11/1985 | Eagon et al. . | |
| 4,556,146 | 12/1985 | Swanson et al. . | |
| 4,581,027 | 4/1986 | Alvarado . | |
| 4,608,047 | 8/1986 | Mattingly . | |
| 4,735,316 | 4/1988 | Froidh et al. . | |
| 4,738,678 | 4/1988 | Paulis . | |
| 4,755,421 | 7/1988 | Manning et al. . | |
| 4,765,477 | 8/1988 | Froidh et al. . | |
| 4,781,712 | 11/1988 | Barabino et al. . | |
| 4,790,670 | 12/1988 | Barbaro | 383/210 |
| 4,846,828 | 4/1989 | Mendelsohn . | |
| 4,857,066 | 8/1989 | Allison . | |
| 4,917,675 | 4/1990 | Taylor et al. . | |
| 5,018,625 | 5/1991 | Focke et al. | 206/494 |
| 5,088,993 | 2/1992 | Gaur . | |
| 5,133,457 | 7/1992 | Kadel . | |
| 5,147,346 | 9/1992 | Cancio et al. . | |
| 5,147,347 | 9/1992 | Huang et al. . | |
| 5,181,610 | 1/1993 | Quick et al. | 383/210 |

FOREIGN PATENT DOCUMENTS

| | | | |
|---|---|---|---|
| 0299532A2 | 1/1989 | European Pat. Off. . | |
| 0313426A1 | 4/1989 | European Pat. Off. . | |
| 0350924A3 | 1/1990 | European Pat. Off. . | |
| 0357000A1 | 3/1990 | European Pat. Off. . | |
| 603211 | 9/1939 | Fed. Rep. of Germany | 206/440 |
| 3324490 | 11/1984 | Fed. Rep. of Germany | 206/494 |
| 640801 | 7/1928 | France | 206/440 |
| WO89/02729 | 9/1987 | PCT Int'l Appl. . | |
| WO89/02728 | 4/1989 | PCT Int'l Appl. . | |

*Primary Examiner*—David Brown

[57] ABSTRACT

An improved fold and wrap package providing containment of a catamenial pad prior to its use and for conveniently disposing of a soiled catamenial pad. The fold and wrap package comprises a wrapper comprising a single strip of material having a flap panel, a central panel, and an end panel; and preferably a tape tab for securing the wrapper in a disposal configuration to provide convenient disposal of a soiled catamenial pad wrapped in the wrapper. The fold and wrap package is initially configured to have a pouch and a flap. The pouch is formed by folding the end panel back upon the central panel and frangibly bonding the end panel to the central panel at the longitudinal edges so that the end panel may be easily peeled away from the central panel to provide convenient disposal of a soiled catamenial pad. The pouch is designed so that an unused catamenial pad may be disposed within the pouch with the flap being positioned over the mouth of the pouch and frangibly bonded to the pouch to securely close the pouch prior to use.

7 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FOLD AND WRAP PACKAGE FOR CATAMENIAL PADS PROVIDING CONVENIENT DISPOSAL

FIELD OF THE INVENTION

This invention is directed to individually packaged catamenial pads and methods for their disposal and, more particularly, to fold and wrap packages for catamenial pads and methods for using such packages to conveniently dispose of soiled catamenial pads.

BACKGROUND OF THE INVENTION

Catamenial pads used to collect vaginal discharges are well known in the art. An important feature of such catamenial pads is they are "sanitary" in that they should not be soiled or contaminated prior to use. This is a particular problem for "away from home" use of catamenial pads. A woman carries the catamenial pads in her purse, briefcase, or pocket until they are ready to be used. Thus, there is the issue of protecting the catamenial pad until it is needed.

In order to protect catamenial pads and provide the convenience of away from home usage, individually packaged catamenial pads have been developed. Individually packaged catamenial pads are disclosed, for example, in U.S. Pat. No. 3,973,567 issued to Srinivasan, et al. on Aug. 10, 1976; U.S. Pat. No. 4,917,675 issued to Taylor, et al. on Apr. 17, 1990; European Patent Application Publication No. 0 357 000 Al published in the name of Umesh on Mar. 7, 1990; and in U.S. Pat. No. 4,556,146 issued Dec. 3, 1985, to Swanson. The Swanson patent discloses a tri-folded wrapper which packages a catamenial pad, covers adhesive on the outwardly oriented face of the catamenial pad, and may be used for disposing of the used catamenial pad.

Another issue with away from home use of catamenial pads is the ability to neatly and discretely dispose of a soiled catamenial pad. Often a woman may have to wrap the catamenial pad in tissue and carry the soiled pad to a proper waste receptacle or back to the home. In order to provide more convenient disposal of soiled catamenial pads, packaging has been developed which allows the soiled catamenial pad to be wrapped in the package which entire system (package and pad) is then thrown away.

Discarding soiled catamenial pads enveloped in its packaging is disclosed, for example, in International Publication WO89/02729 published Aug. 6, 1989 in the name of Pigneul; U.S. Pat. No. 4,608,047 issued Aug. 26, 1986 to Mattingly; and U.S. Pat. 4,556,146 issued Dec. 3, 1985, to Swanson.

One type of packaging developed for such uses is the so called "fold and wrap" package. The fold and wrap package has a pouch into which an unused catamenial pad is folded and placed. A flap covers the mouth of the pouch to protect the unused catamenial pad. The wearer opens the flap and removes the unused catamenial pad. A soiled catamenial pad may then be rolled up, placed into the pouch, and the flap repositioned over the mouth of the pouch for disposal of both the package and the soiled catamenial pad.

However, this type of "fold and wrap" package has several drawbacks. First, the soiled catamenial pad needs to be tightly folded or wrapped prior to insertion into the pouch in order that it will fit into the pouch. This may cause fluid to leak out of the pad onto the wearer. It is also difficult to insert the soiled catamenial pad into the pouch because the adhesive used to attach the pad to the undergarment sticks to the pouch. Further, the initial flap seal provided on the pouch may not reseal to hold the flap in place over the mouth of the pouch. During transport, the flap may open allowing the soiled catamenial pad to fall out of the pouch or fluid to leak out to the surrounding environment.

Thus, there is a need to provide an improved fold and wrap package that provides convenient and "secure" disposal of a soiled catamenial pad.

Accordingly, it is an object of the present invention to provide a fold and wrap package for catamenial pads that is easy for the user to open and remove an unused catamenial pad, and provides convenient and secure disposal of a soiled catamenial pad.

SUMMARY OF THE INVENTION

The present invention relates to an improved fold and wrap package providing containment of a catamenial pad prior to its use and for conveniently disposing of a soiled catamenial pad. The fold and wrap package comprises a wrapper comprising a single strip of material having a flap panel, a central panel, and an end panel; and a disposal means, typically a tape tab, for securing the wrapper in a disposal configuration to provide convenient disposal of a soiled catamenial pad wrapped in the wrapper. The fold and wrap package is initially configured to have a pouch and a flap. The pouch is formed by folding the end panel back upon the central panel and frangibly bonding the end panel to the central panel at the longitudinal edges so that the end panel may be easily peeled away from the central panel to provide convenient disposal of a soiled catamenial pad. The pouch is designed so that an unused catamenial pad may be disposed within the pouch with the flap being positioned over the mouth of the pouch and frangibly bonded to the pouch to securely close the pouch prior to use.

The fold and wrap package is used by peeling the tape tab from the pouch, peeling the flap away from the pouch by breaking the frangible bonds between the flap and the pouch, removing the unused catamenial pad from the pouch, peeling the end panel from the central panel to open the pouch such that the fold and wrap package is a flat wrapper (these previous two steps may also be done in reverse order), securing a soiled catamenial pad to the wrapper, disposing the wrapper and the soiled catamenial pad into a disposal configuration, and securing the wrapper and the soiled catamenial pad in its disposal configuration by securing the tape tab to another portion of the wrapper.

BRIEF DESCRIPTION OF THE DRAWINGS

While the specification concludes with claims particularly pointing out and distinctly claiming the present invention, it is believed the invention will be better understood from the following description taken in conjunction with the accompanying drawings wherein like parts are given the same reference numeral, and:

DETAILED DESCRIPTION OF THE INVENTION

Figure 1:
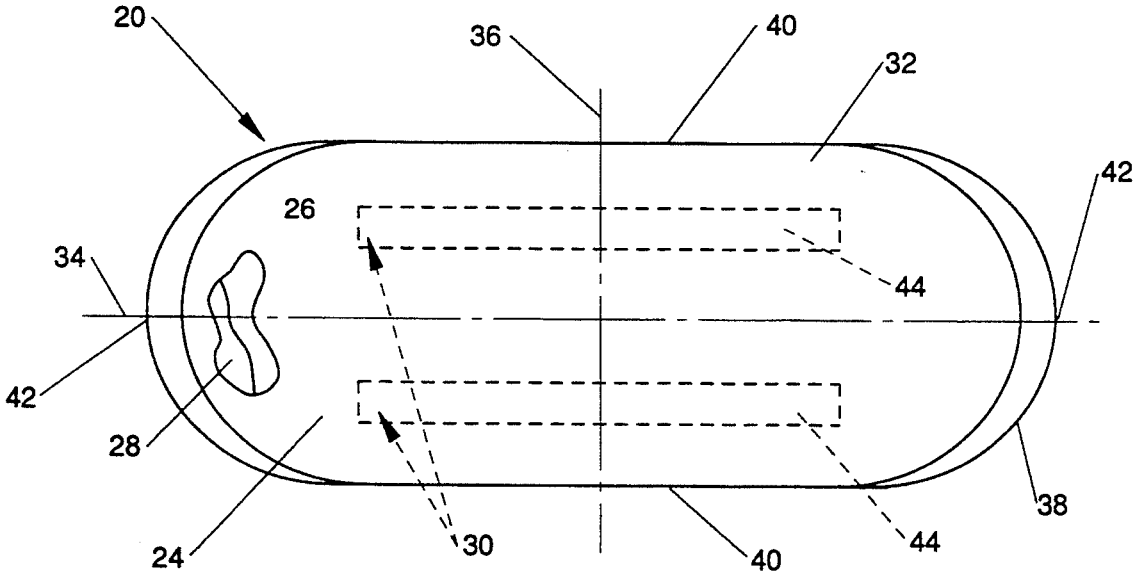
FIG. 1 is a partially cut-away top plan view of a catamenial pad useful with the present invention.

The present invention is directed to a fold and wrap package for use with an absorbent article such as a catamenial pad as shown in FIG. 1 and the method for using the same.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A preferred embodiment of a disposable absorbent article of the present invention is the catamenial pad 20 shown in FIG. 1. As used herein, the term "catamenial pad" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene pads or other absorbent articles such as incontinence pads, and the like.

FIG. 1 is a plan view of the catamenial pad 20 of the present invention in its flat-out state with portions of the structure being cut-away to more clearly show the construction of the catamenial pad 20 and with the portion of the catamenial pad 20 which faces or contacts the wearer, oriented towards the viewer. As shown in FIG. 1, the catamenial pad 20 preferably comprises a liquid pervious topsheet 24, a liquid impervious backsheet 26 joined with the topsheet 24, an absorbent core 28 positioned between the topsheet 24 and the backsheet 26, panty fastening members 30, and a release liner (not shown).

The catamenial pad 20 has two surfaces, a body-contacting surface or "body surface" 32 and a garment surface 34. The catamenial pad 20 is shown in FIG. 1 as viewed from its body surface 32. The body surface 32 is intended to be worn adjacent to the body of the wearer while the garment surface 34 is on the opposite side and is intended to be placed adjacent to the wearer's undergarments when the catamenial pad 20 is worn. The catamenial pad 20 has two centerlines, a longitudinal centerline 34 and a transverse centerline 36. The term "longitudinal", as used herein, refers to a line, axis or direction in the plane of the catamenial pad 20 that is generally aligned with (e.g., approximately parallel to) a vertical plane which bisects a standing wearer into left and right body halves when the catamenial pad 20 is worn. The terms "transverse" or "lateral" as used herein, are interchangeable, and refer to a line, axis or direction which lies within the plane of the catamenial pad 20 that is generally perpendicular to the longitudinal direction. FIG. 1 also shows that the catamenial pad 20 has a periphery 38 which is defined by the outer edges of the catamenial pad 20 in which the longitudinal edges are designated 40 and the end edges are designated 42.

While the topsheet 24, the backsheet 26, and the absorbent core 28 may be assembled in a variety of well known configurations (including so called "tube" products or side flap products), preferred catamenial pad configurations are described generally in U.S. Pat. No. 4,950,264, "Thin, Flexible Sanitary Napkin" issued to Osborn on Aug. 21, 1990; U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 5,171,302, "Absorbent Article With Central Hinge" issued to Buell on Dec. 15, 1992; U.S. Pat. No. 4,738,676, "Pantliner" issued to Osborn on Apr. 19, 1988; and U.S. Pat. No. 4,589,876, "Shaped Sanitary Napkin With Flaps" issued to Van Tilburg on Aug. 18, 1987. Each of these patents are hereby incorporated herein by reference.

The absorbent core 28 may be any absorbent means which is capable of absorbing or retaining liquids (e.g., menses and/or urine). The absorbent core 28 may be manufactured in a wide variety of sizes and shapes (e.g., rectangular, oval, hourglass, dog bone, asymmetric, etc.) and from a wide variety of liquid-absorbent materials commonly used in catamenial pads and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the catamenial pad 20. Further, the size and absorbent capacity of the absorbent core may be varied to accommodate different uses such as incontinence pads, pantiliners, regular sanitary napkins, or overnight catamenial pads.

Exemplary absorbent structures for use as the absorbent core 28 of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sept. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 26 and the topsheet 24 are positioned adjacent the garment surface and the body surface, respectively, of the absorbent core 28 and are preferably joined thereto and to each other by chassis attachment means (not shown) such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The chassis attachment means preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary chassis attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the chassis attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the catamenial pad 20 such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet 26 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Corporation of Terre Haute, Ind., under the designation XP-39385. The backsheet is preferably embossed and/or matte finished to provide a more clothlike appearance. Further, the backsheet may permit vapors to escape from the absorbent core (i.e., breathable) while still preventing exudates from passing through the backsheet.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet 24 for the present invention is the formed film described in one or more of the above patents and marketed on catamenial pads by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. 4,950,254 issued to Osborn, incorporated herein by reference.

In use, the catamenial pad 20 can be held in place by any support means or attachment means (panty fastening member 30) well-known for such purposes. For example, the panty fastening member 30 may comprise a mechanical fastener such as hook and loop fasteners such as marketed under the tradename VELCRO, snaps, or holders. Preferably, the catamenial pad is placed in the user's undergarment or panty and secured thereto by a panty fastening member 30 such as an one or more areas of an adhesive (panty fastening adhesive 44) coated onto the backsheet 26. The panty fastening adhesive 44 provides a means for securing the catamenial pad 20 in the crotch portion of the panty, and preferably, for purposes of this invention, a means for securing the catamenial pad 20, when soiled, to the fold and wrap package for convenient disposal. Thus, a portion or all of the outer surface of the backsheet 26 may be coated with adhesive to form the panty fastening adhesive 44. Any adhesive or glue used in the art for such purposes can be used for the panty fastening adhesive 44 herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable panty fastening members 30, particularly panty fastening adhesives 44, are also described in the above-referenced U.S. Pat. No. 4,917,697.

Before the catamenial pad 20 is placed in use, the panty fastening adhesive 44 is typically covered with a removable release liner (not shown) in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The catamenial pad 20 of the present invention is used by removing the release liner and thereafter placing the catamenial pad 20 in a panty so that the panty fastening adhesive 44 contacts the panty. The panty fastening adhesive 44 maintains the catamenial pad 20 in its position within the panty during use.

In an alternative embodiment of the present invention, the catamenial pad has two flaps each of which are adjacent to and extend laterally from the side edge of the absorbent core. The flaps are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with panty fastening members on their garment surface so that the flaps can be folded back under the panty and attached to the garment facing side of the panty. In this way, the flaps serve to keep the catamenial pad properly positioned in the panty. The flaps can be constructed of various materials including materials similar to the topsheet, the backsheet, or combination of these materials. Further, the flaps may be a separate element attached to the main body of the napkin or can comprise extensions of the topsheet and the backsheet (i.e., unitary). A number of catamenial pads having flaps suitable or adaptable for use with the catamenial pads of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. Each of these patents are incorporated herein by reference.

In an alternative embodiment of the present invention, an acquisition layer(s) may be positioned between the topsheet and the absorbent core. The acquisition layer may serve several functions including improving wicking of exudates over and into the absorbent core. There are several reasons why the improved wicking of exudates is important, including providing a more even distribution of the exudates throughout the absorbent core and allowing the catamenial pad to be made relatively thin. (The wicking referred to herein may encompass the transportation of liquids in one, two or all directions (i.e, in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of catamenial pads having an acquisition layer and a topsheet are more fully described in U.S. Pat. No. 4,950,264 issued to Osborn and U.S. patent application Ser. No. 07/810,774, "Absorbent Article Having Fused Layers", filed by Cree, et al. on Dec. 17, 1991. Each of these references are incorporated herein by reference. In a preferred embodiment, the acquisition layer may be joined with the topsheet by any of the conventional means for joining webs together, most preferably by fusion bonds as is more fully described in the above-referenced Cree application.

Figure 2:
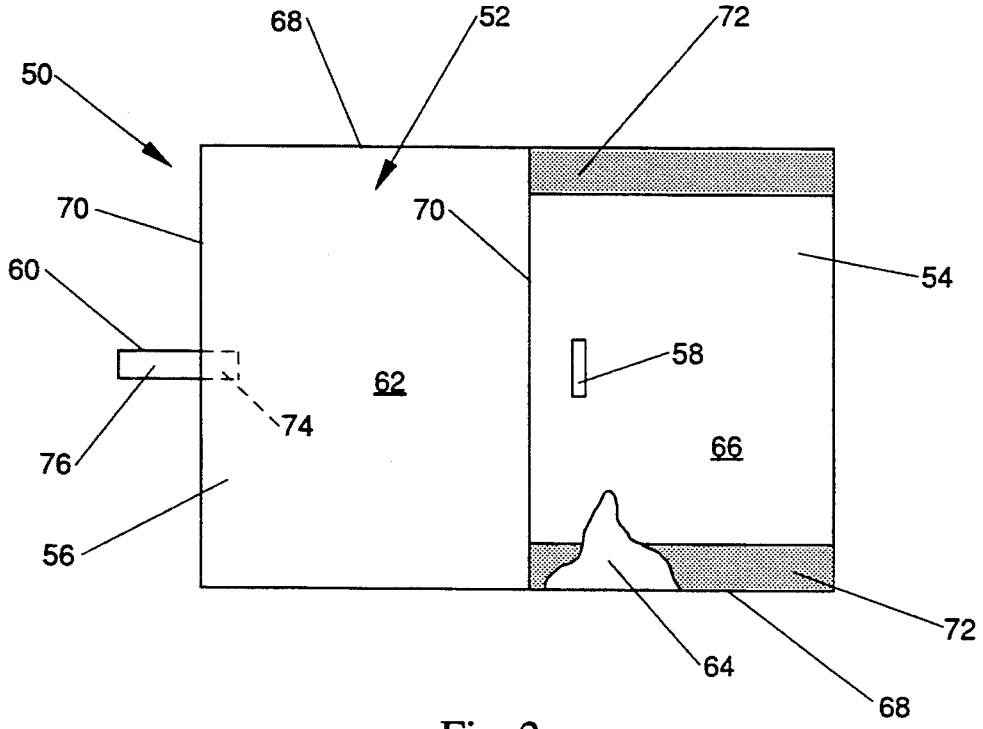
FIG. 2 is a partially cut-away top plan view of the fold and wrap package according to the present invention in its flat out state prior to insertion of a catamenial pad into the pouch.

The package shown in FIG. 2 is referred to as "fold and wrap" package 50. The fold and wrap package 50 is a discrete package for containing a catamenial pad prior to use and for conveniently disposing of a soiled catamenial pad. The fold and wrap package 50 of the present invention preferably comprises a wrapper 52 comprising a single strip of material configured to initially provide a pouch 54 and a flap 56; a pouch closure member 58; and a disposal means for securing the wrapper with a soiled catamenial pad contained therein in a disposal configuration, the disposal means as shown in FIG. 2 preferably comprising the tape tab 60. The wrapper 52 forms the main body of the fold and wrap package 50 and has a flap panel 62, a central panel 64 contiguous with the flap panel 62, an end panel 66 contiguous with the central panel 64, a pair of longitudinal edges 68, and a pair of end edges 70. In its initial configuration, the wrapper 52 is configured to provide a pouch 54 comprising the central panel 64 and the end panel 66, and a flap 56 contiguous with the pouch 54. The pouch 54 is formed by folding the end panel 66 back upon the central panel 64 and frangibly bonding the end panel 66 to the central panel 64 along the longitudinal edges 68 of the wrapper 52 to form frangible bonds 72 so that a closed end pouch is formed having three side walls and an open mouth. The frangible bonds 72 between the end panel 66 and the central panel 64 also allow the end panel 66 to be peeled away from the central panel 64 to place the wrapper 52 in a convenient disposal configuration for a soiled catamenial pad. The flap 56 is formed by at least the flap panel 62 which extends beyond the mouth of the pouch 54. The flap 56 is designed to fold over the mouth of the pouch 54 to secure the catamenial pad within the pouch 54 and protect it from being contaminated prior to use. The flap 56 is frangibly bonded to the pouch 54 along the longitudinal edges 68 of the wrapper 52 so that the flap 56 may be opened to remove the unused catamenial pad and provide a disposal configuration of a soiled catamenial pad. FIG. 2 shows the fold and wrap package 50 in an open state prior to insertion of a folded unused catamenial pad into the pouch 54.

Figure 3:
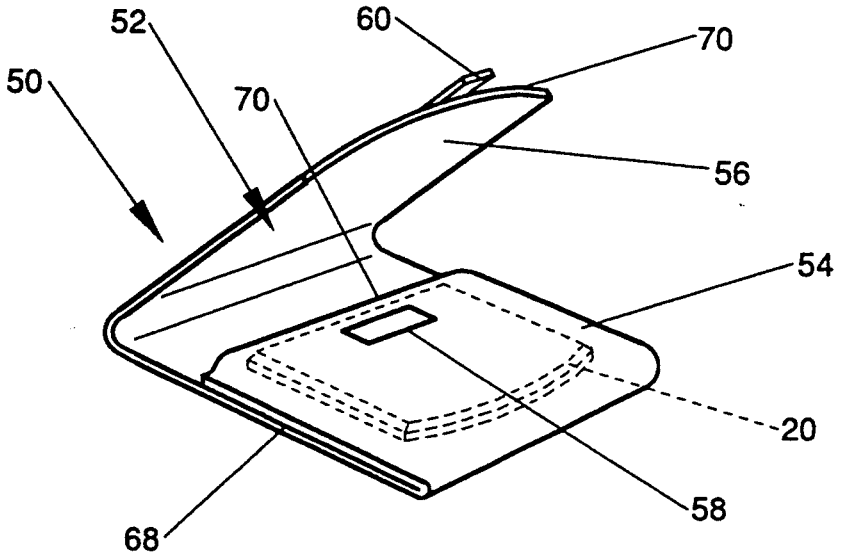
FIG. 3 is a perspective view of the catamenial pad of FIG. 1 in a folded configuration placed within the pouch of the fold and wrap package prior to use by the wearer with the flap folded over the mouth of the pouch.

FIG. 3 shows a perspective view of the fold and wrap package 50 of the present invention having an unused catamenial pad 20 contained within the pouch 54. As shown in FIG. 3, the catamenial pad 20 is folded and disposed into the pouch 54 to hold the catamenial pad 20 in place. The catamenial pad 20 is typically folded about at least one axis, preferably about two fold axes, so that the topsheet is protected from soiling. The catamenial pad has the garment surface on the outside with the release liner covering the panty fastening adhesive. The flap 56 of the fold and wrap package 50 is shown in a folded configuration to close the mouth of the pouch 54 but prior to the flap 56 being frangibly bonded to the pouch 54. The pouch closure member 58 is shown in FIG. 3 as being ready to adhere the flap 56 to the pouch 54 to provide an even more secure closure for the fold and wrap package 50 prior to use. Preferably, the tape tab 60 is also secured to the end panel 66 of the pouch 54 to close the flap 56 so that foreign objects may not get under the flap 56 and into the pouch 54, although the disposal means, preferably the tape tab 60, need not be used to secure the fold and wrap package initially closed such that it may be saved for use only with a soiled catamenial pad.

Figure 4:
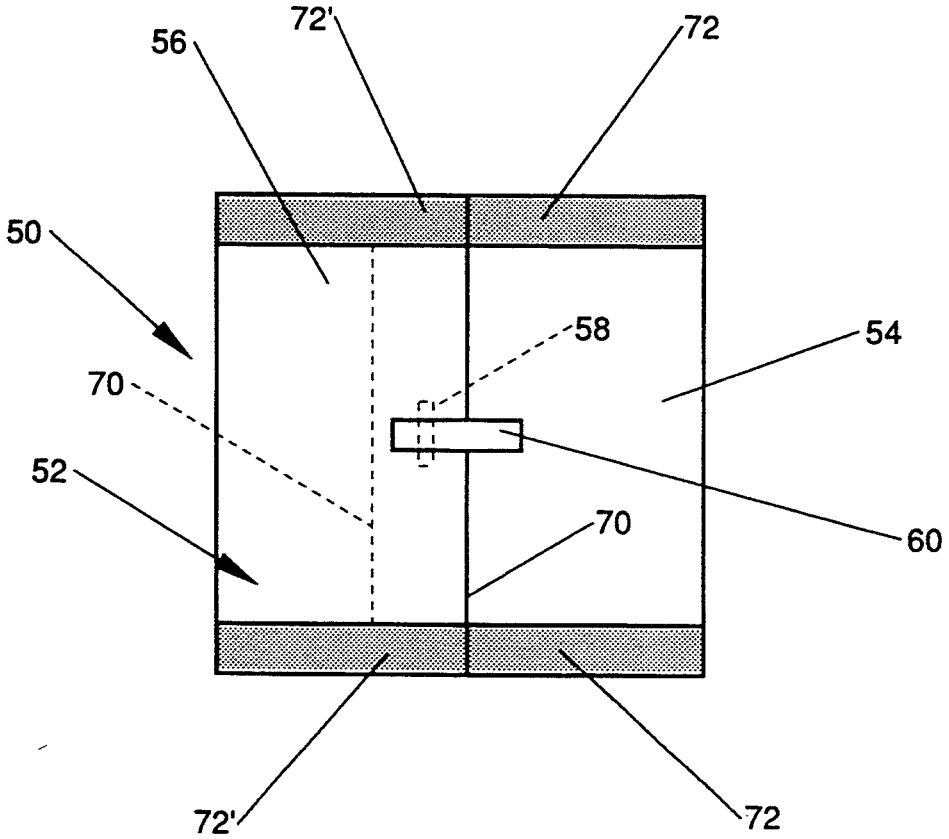
FIG. 4 is a top plan view of the fold and wrap package in its final configuration for carrying with the user.

FIG. 4 is a top plan view of the fold and wrap package/catamenial pad unit in its configuration as provided by the manufacturer for convenient use by the wearer. As shown in FIG. 4, the flap 56 has been folded over onto the pouch 54 and secured thereto by at least the pouch closure member 58 and, preferably, by the tape tab 60 . Further, the flap 56 has been frangibly bonded to the pouch 54 along the longitudinal edges 68 by frangible bonds 72'.

During use, the tape tab 60 is peeled away from the end panel 66 of the pouch 54. Then, the frangible bonds 72' between the flap 56 and the pouch 54 are broken, without degrading or tearing the material of the wrapper 52, to open the flap 56. Finally, the flap 56 is peeled or torn away from the pouch closure member 58. The fold and wrap package 50 will thus again assume the configuration such as is shown in FIG. 3.

The unused catamenial pad is then typically removed from the pouch 54, although the catamenial pad can be removed after the pouch has been broken open as described below. The catamenial pad is unfolded or unrolled, the release liner is removed from the panty fastening adhesive, and the panty fastening adhesive is secured to the undergarment of the wearer for use of the catamenial pad. The fold and wrap package 50 then again assumes the configuration shown in FIG. 2.

Figure 5:
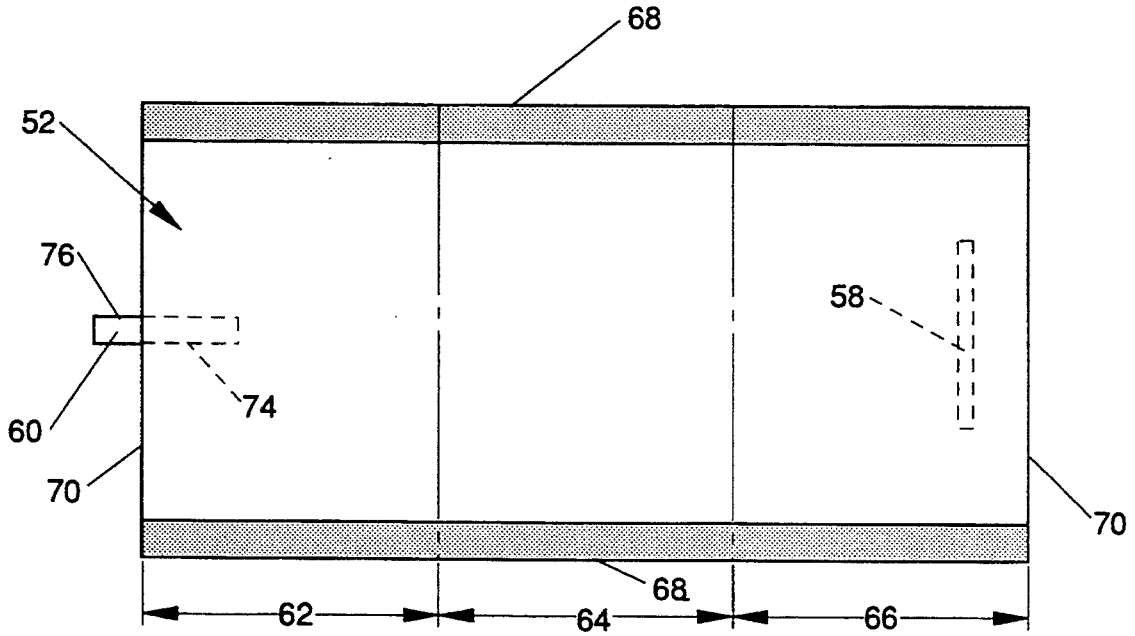
FIG. 5 is a top plan view of the fold and wrap package after the catamenial pad has been removed from the pouch and the end panel has been peeled away from the central panel to open the pouch.

The end panel 66 is then peeled away from the central panel 64 by breaking, without degrading or tearing the material of the wrapper 52, the frangible bonds 72 between the end panel 66 and the central panel 64. FIG. 5 shows a top plan view of the fold and wrap package 50 in its initial disposal configuration with the end panel 66 peeled away from the central panel 64 such that a flat strip of material (the wrapper 52) is provided with the tape tab 60 at the end edge 70 adjacent the flap panel 62. (As discussed above, the catamenial pad can alternatively be removed from the fold and wrap package 50 after this step.)

Figure 6:
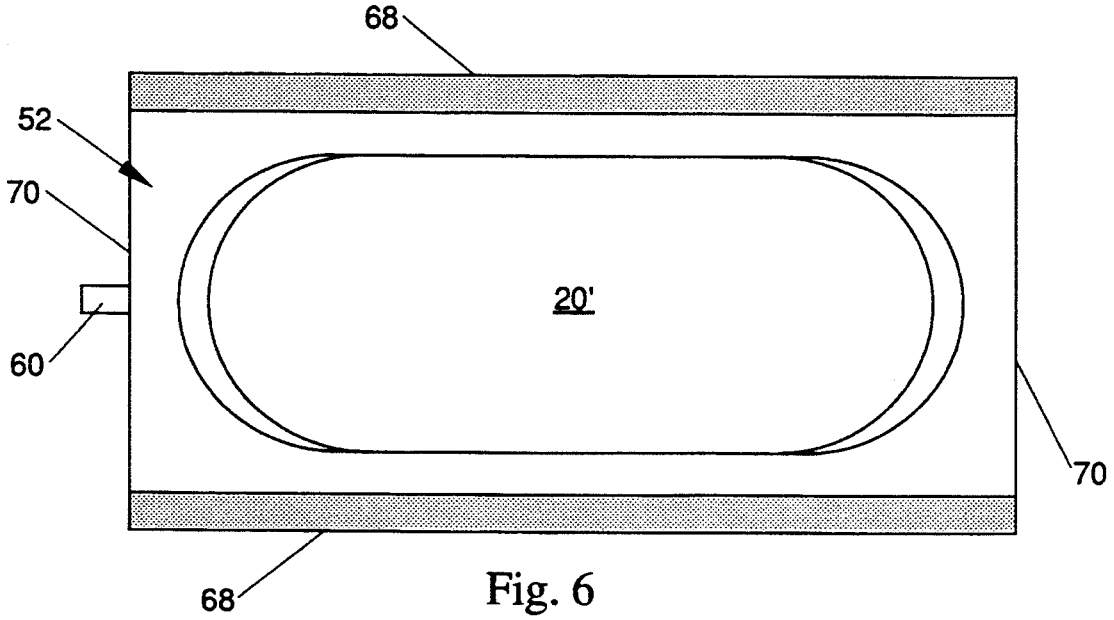
FIG. 6 is a top plan view of a soiled catamenial pad and an opened fold and wrap package showing the catamenial pad adhered to the fold and wrap package prior to being configured for disposal.

FIG. 6 shows the opened fold and wrap package with a soiled catamenial pad 20' secured to the wrapper 52. Preferably, the panty fastening adhesive used for attaching the catamenial pad to the undergarment of the wearer is used to attach the soiled catamenial pad to the fold and wrap package. The soiled catamenial pad may alternatively be disposed in other configurations (such as rolled up) and placed on or attached to the wrapper 52. The entire package unit (wrapper and soiled catamenial pad) is then rolled or folded into a disposal configuration.

Figure 7:
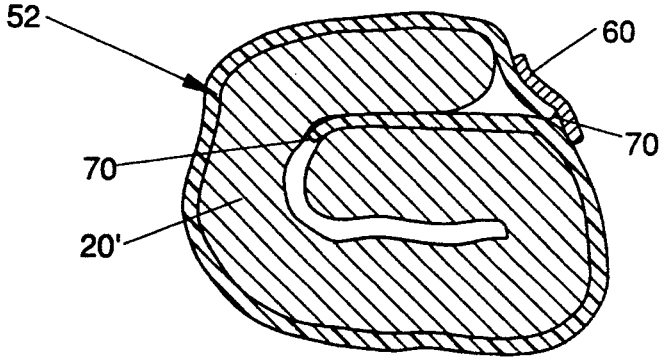
FIG. 7 is a simplified side view of a soiled catamenial pad and fold and wrap package secured in its disposal configuration by the tape tab.

FIG. 7 shows a typical disposal configuration for the package unit of the wrapper 52 and the soiled catamenial pad 20'. In this embodiment, the package unit of FIG. 6 is rolled from the end panel 66 toward the flap panel 62 such that the soiled catamenial pad 20' is contained within the wrapper 52. The tape tab 60 is then secured to the outer portions of the wrapper 52 to secure the package unit (the soiled catamenial pad 20' and the wrapper 52) in a disposal configuration. This package unit may then be conveniently disposed of in a waste receptacle.

The single strip of material (wrapper 52) forming the fold and wrap package 50 may comprise a number of materials. The wrapper 52 is preferably made of those materials that will prevent contamination of an unused catamenial pad and leakage from a soiled catamenial pad. Preferably, the wrapper 52 is a relatively thin flexible material to allow the fold and wrap package to be easily folded and frangibly bonded along its longitudinal edges. Preferably, and since only frangible bonds are used, the material may be any thin, preferably liquid impervious, more preferably polymeric material as are known in the art. In a preferred embodiment, the fold and wrap material comprises a thin (preferably about 1 mil (0.025 mm)) monolayer polyethylene blend film, such as those suitable for use as the backsheet 26 including the film marketed by Tredegar under the designation X-9313. Alternatively, the wrapper 52 can be made of other films, kraft paper, calendered paper, or laminated materials of one or more layers or sheets of material.

As discussed herein, the longitudinal edges 68 of the wrapper 52 are frangibly bonded together to form a pouch 54 and a closed fold and wrap package such as is shown in FIG. 4. As used herein, the term "frangibly bonded" refers to a bond that may be opened or broken easily by the wearer during use without significant, preferably no, destruction (ripping or tearing) or undue distortion to either component frangibly bonded together. The frangible bonding can be done using any of a number of well-known sealing techniques. For example, the frangible bonds 72 or 72' may be formed by crimping. heat seals, adhesives, mechanical fasteners such as hook and loop fasteners such as are sold under the tradename VELCRO, or ultrasonic bonds. Alternatively, frangible bonds can be formed by zippered track sealing systems such as Dow Chemical Chemical Company's "ZIPLOCKS". Preferably, the wrapper 52 is frangibly bonded along the longitudinal edges 68 in accordance with the teachings of U.S. Pat. No. 4,556,146 issued to Swanson, et al. on Dec. 3, 1985, which patent is incorporated herein by reference, more preferably by crimping the longitudinal edges 68 to provide a peelable crimped seal.

The fold and wrap package 50 is also preferably provided with a pouch closure member 58 for sealing the flap 56 to the pouch 54 prior to use of the catamenial pad. Alternatively, the fold and wrap package need not comprise a pouch closure member or the pouch closure member could act as the disposal means itself without the need for additional elements. The pouch closure member 58 may be positioned adjacent the mouth of the pouch 54, or at some other position along the length of the pouch 54. The pouch closure member 58 may comprise any suitable type of sealing means, including, but not limited to adhesives, zippered track sealing systems, hook and loop fasteners, or tear seals. Preferably, the pouch closure member 58 comprises a patch of pouch seal adhesive, such as the adhesives capable for use as the chassis attachment means, which pouch seal adhesive is disposed on the end panel preferably in a spiral pattern.

The fold and wrap package 50 is also provided with a disposal means for securing the wrapper with the soiled catamenial pad contained within it in a disposal configuration; and, preferably, also for providing closure of the flap 56 prior to the first use of the catamenial pad. In alternative embodiments, the disposal means is not used for holding the package initially closed (i.e., it may be preserved for retaining the package unit when disposing of a soiled catamenial pad). Thus, the disposal means may be any structure that allows the wrapper to be folded or rolled up into a configuration for disposal and secured in that configuration to contain the soiled catamenial pad within the wrapper. Thus, for example, the disposal means may comprise a number of different elements positioned on and/or joined to the wrapper such as tape tabs (either adhesive tape tabs or mechanical tape tabs), adhesive attachment means, mechanical fastening elements, a hook fastening material, a loop fastening material, or any other element or combination of elements readily known to those of skill in the art. Examples of disposal means adaptable for use with the present invention are disclosed in U.S. Pat. No. 4,963,140, entitled "Mechanical Fastening Systems With Disposal Means For Disposable Absorbent Articles" issued to Anthony J. Robertson and Charles L. Scripps on Oct. 16, 1990; which patent is incorporated herein by reference.

The disposal means may be positioned anywhere on wrapper 52 so long as it secures the wrapper and the soiled catamenial pad in a configuration for disposal. For example, the disposal means may be positioned on either surface of the end panel 66, on either surface of the central panel 64, or on either surface of the flap panel 62. Preferably, the disposal means is positioned in the flap panel 62, more preferably adjacent the end edge 70 in the flap panel 62.

Preferred disposal means comprise a tape tab positioned to allow for convenient disposal of the wrapper and the soiled catamenial pad. The tape tab 60 preferably comprises any tape tab known in the art used for sealing articles together. The tape tab 60 preferably comprises a fixed portion 74 and a connective portion 76 extending outwardly from the end edge 70 of the flap panel 62. The tape tab 60 may comprise any of the attachment means known in the art such as adhesive tape tabs, mechanical fastener tape tabs, and the like. Preferred materials for the tape tabs comprise a tape material such as tape Code Numbers XPF14.43.0, Y-9376, or Y9030 available from the Minnesota Mining and Manufacturing Company, St. Paul, Minn. Particularly preferred tape tabs are disclosed in U.S. patent application Ser. No. 07/795,932, entitled "Sanitary Napkin Wrapper and Adhesive Tab Construction For The Same" filed by Charles J. Berg, et al. on Nov. 15, 1991; and U.S. patent application Ser. No. 07/934,147, entitled "Refastenable Adhesive Fastening Systems For Individually Packaged Disposable Absorbent Articles" filed by Jennifer A. Roach, et al. on Aug. 21, 1992; which patent applications are incorporated herein by reference. An exemplary tape tab not used for initially securing the flap closed is disclosed in U.S. patent application Ser. No. 07/874,871, entitled "Individually Packaged Sanitary Napkin Having Cleansing Wipe Packaged Therewith" filed by Daniella J. Fischer, et al. on Apr. 28, 1992; which patent application is incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fold and wrap package for containing a catamenial pad prior to use and for conveniently and securely disposing of a soiled catamenial pad, said fold and wrap package comprising:

a wrapper having a flap panel, a central panel contiguous with said flap panel, an end panel contiguous with said central panel, longitudinal edges, and end edges, said wrapper being initially configured to provide:

a pouch comprising said central panel and said end panel, said pouch formed by folding said end panel back upon said central panel and frangibly bonding said end panel to said central panel at said longitudinal edges by frangible bonds so that said end panel may be peeled away from said central panel to provide disposal of a soiled catamenial pad, said pouch being capable of receiving an unused catamenial pad; and a flap contiguous with said pouch, said flap having a distal end defined by one of said end edges, said flap being formed by said flap panel, said flap panel being folded back upon said end panel to close said pouch, said flap panel being frangibly bonded to said pouch along said longitudinal edges by frangible bonds so that said flap may be peeled away from said pouch to open said pouch to allow removal of an unused catamenial pad and provide disposal of a soiled catamenial pad; and a tape tab positioned adjacent said distal end of said flap for securing said wrapper and a soiled sanitary napkin secured thereto in a disposal configuration.

2. The fold and wrap package of claim 1 additionally comprising a pouch closure member disposed on said end panel for releasably securing said flap to said pouch.

3. The fold and wrap package of claim 1 wherein said tape tab comprises an adhesive tape tab.

4. The fold and wrap package of claim 3 wherein said wrapper comprises a single layer of polyethylene film.

5. The fold and wrap package of claim 4 wherein said frangible bonds comprise peelable crimped seals.

6. The fold and wrap package of claim 5 additionally comprising a pouch closure member disposed on said end panel for releaseably securing said flap to said pouch.

7. The fold and wrap package of claim 6 wherein said pouch closure member comprises adhesive.

* * * * *